(12) United States Patent
Harland et al.

(10) Patent No.: US 6,432,410 B1
(45) Date of Patent: *Aug. 13, 2002

(54) MORPHOGENIC PROTEINS

(75) Inventors: Richard Harland; David Hsu, both of Berkeley, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1 days.

(21) Appl. No.: 09/040,229

(22) Filed: Mar. 13, 1998

Related U.S. Application Data

(63) Continuation of application No. 08/795,501, filed on Feb. 5, 1997, now abandoned.

(51) Int. Cl.$^7$ .......................... A61K 38/16; A61K 38/18
(52) U.S. Cl. .......................... 424/198.1; 514/12; 514/21
(58) Field of Search .............................. 424/130.1, 94.1, 424/198.1; 514/221

(56) References Cited

U.S. PATENT DOCUMENTS 5,674,844 A * 10/1997 Kubersampath et al.
5,935,852 A * 8/1999 Follettie et al. ............. 435/325

OTHER PUBLICATIONS

Demetriou et al., J Biol Chem 271(22):12755–61, 1996.*
Skolnick et al., Trends in Biotech 18(1):34–39, 2000.*
Wu et al., J. of Cell Physiol., 168(2):453–61, 1996.*
Bouwmeester et al., Nature 382:595–601, 1996.*
Ozaki et al., PNAS 90:2593–97, 1993.*
Nakamura et al., Eur. J. of Cancer 33(12):1986–90, 1997.*
Marinova–Mutafchieva et al., Bone, 27(3):453–59, 2000.*
Raoch, Bone 27(3):453–59, 2000.*
Rudinger, University Park Press, p. 1–7, 1988.*
Miyata et al, Br. J. of Haematol., 1994, 88, 156–65, 1994.*
L. Hillier et al. The WashU–Merck EST Project. EMBL Sequence Database, Jan. 19, 1996. Accession No. N35377.
L. Hillier et al. The WashU–Merck EST Project. EMBL Sequence Database, Dec. 16, 1995. Accession No. H99469.

* cited by examiner

*Primary Examiner*—Gary L. Kunz
*Assistant Examiner*—Sharon Turner
(74) *Attorney, Agent, or Firm*—Richard Aron Osman

(57) ABSTRACT

DAN (Differential-screening-selected gene Aberrative in Neuroblastoma) and gremlin proteins and related nucleic acids are provided. Included are natural DAN and gremlin homologs from several species and proteins comprising a DAN or gremlin domain having specific activity, particularly the ability to antagonize a bone morphogenic protein. The proteins may be produced recombinantly from transformed host cells with the subject nucleic acids. Also provided are isolated hybridization probes and primers capable of specifically hybridizing with the disclosed genes, specific binding agents and methods of making and using the subject compositions.

20 Claims, 1 Drawing Sheet

FIG. 1A

```
xGremlin  MNCLVYALGSLFLLSGLLLPSSEGKKKVSGSQGAIPPPDKGQPNDSEQGQ   50
cGremlin  MVRTLYAIGAVFLLTGFLLPTAEGRKRNRGSQGAIPPPDKDQPNDSEQMQ   50
mGremlin  MNRTAYTVGALLLLLGTLLPTAEGKKK..GSQGAIPPPDKAQHNDSEQTQ   48
hGremlin  MSRTAYTVGALLLLLGTLLPAAEGKKK..GSQGAIPPPDKAQHNDSEQTQ   48
                                                        *
xGremlin  A..QPG..DRVRGKGKGQALAAEEVLESSQEALHVTERKYLKRDWCKTQP   96
cGremlin  TQQQSGSRHRERGKGT..SMPAEEVLESSQEALHITERKYLKRDWCKTQP   98
mGremlin  SPPQPGSRTRGRGQGRGTAMPGEEVLESSQEALHVTERKYLKRDWCKTQP   98
hGremlin  SPQQPGSRNRGRGQGRGTAMPGEEVLESSQEALHVTERKYLKRDWCKTQP   98
                  *              *  *                  *  *
xGremlin  LKQTIHEDGCNSRTIINRFCYGQCNSFYIPRHIRREEGSFQSCSFCKPKK  146
cGremlin  LKQTIHEEGCNSRTIINRFCYGQCNSFYIPRHVRKEEGSFQSCSFCKPKK  148
mGremlin  LKQTIHEEGCNSRTIINRFCYGQCNSFYIPRHIRKEEGSFQSCSFCKPKK  148
hGremlin  LKQTIHEEGCNSRTIINRFCYGQCNSFYIPRHIRKEEGSFQSCSFCKPKK  148
                       *                        *  *
xGremlin  FTTMVVTLNCPELQPPTKKKRITRVKQCRCISIDLD  182
cGremlin  FTTMTVTLNCPELQPPRKKKRITRVKECRCISIDLD  184
mGremlin  FTTMMVTLNCPELQPPTKKKRVTRVKQCRCISIDLD  184
hGremlin  FTTMMVTLNCPELQPPTKKKRVTRVKQCRCISIDLD  184
```

FIG. 1B

```
                      *                *             *    *
xGremlin  KRDWCKTQPLKQTIHEDGCNSRTIINRFCYGQCNSFYIPRHIRRE-EGSF  136
xCerberus MKEACKTLPFTQNIVHENCDRMVIQNNLCFGKCISLHVPNQQDRR-N---  210
    mDAN  KSAWCEAKNITQIVGHSGCEAKSIQNRACLGQCFSYSVPNTFPQS-TESL   78
    xDAN  KSAWCEAKNITQIVGHSGCESKSIQNRACLGQCFSYSVPNTFPQS-TESL   79
   ceGR-1 MNQRCDGQKFKQRIRVDGCLTKVVVNRLCHGACASIFIPRMHSKKLKAAF
               *  *         *                      *   *
xGremlin  QSCSFCKPKKFTTMVVTLNCPELQPPTKKKRITR-VKQCRCISIDLD--  182
xCerberus -TCSHCLPSKFTLNHLTLNCTGSKNVVKVVMMVE---ECTCEAHKSNF-  254
    mDAN  VHCDSCMPAQSMWEIVTLECPDHEEVPRVDKLVEKIVHCSCQACGKEP-  126
    xDAN  VHCDSCMPIDSVWDVVTLECPGNEEFPRVDKLVEKILQCSCQACGKEL-  127
   ceGR-1 RSCAACAPAEYDYVDITLDCPGRTPPTATKTIVK-VKSCKCKEVRIAPF
```

MORPHOGENIC PROTEINS

CROSS-REFERENCE TO RELATED APPLICATION

This application is a continuing application under 35USC120 of U.S. Ser. No. 08/795,501 filed Feb. 5, 1997, now abandoned, the specification of which is incorporated by reference.

The research carried out in the subject application was supported in part by grants from the National Institutes of Health. The government may have rights in any patent issuing on this application.

INTRODUCTION

1. Field of the Invention

The field of this invention is proteins which regulate cell function, and in particular, antagonize bone morphogenic proteins.

2. Background

Natural regulators of cellular growth, differentiation and function have provided important pharmaceuticals, clinical and laboratory tools, and targets for therapeutic intervention. A variety of such regulators have been shown to have profound effects on basic cellular differentiation and developmental pathways. For example, the recently cloned cerberus protein induces the formation of head structures in anterior endoderm of vertebrate embryos. Similarly, the noggin protein induces head structures in vertebrate embryos, and can redirect mesodermal fates from ventral fates, such as blood and mesenchyme, to dorsal fates such as muscle and notochord and can redirect epidermal fates to anterior neural fates. The activities of chordin are similar to those of noggin, reflecting a common mechanism of action; namely antagonizing bone morphogenic proteins (BMP) and thereby preventing their function. BMPs have diverse biological activities in different biological contexts, including the induction of cartilage and bone, connective tissue, and roles in kidney, tooth, gut skin and hair development.

Different members of the TGFβ superfamily can instruct cells to follow different fates, for example TGFβ induces neural crest to form smooth muscle, while BMP2 induces the same cells to become neurons. In Xenopus experiments, dissociated animal cap cells (prospective ectoderm) become epidermis in response to BMP4 but become mesoderm in response to activin. Since the identity between activin and BMP4 is low, it is not surprising that they induce different fates. It is more surprising that members of the BMP subfamily, which are quite closely related in sequence, can induce distinct fates. A striking example results from implantation of a matrix impregnated with a BMP into muscle; when the effects are monitored histologically, BMP2, 4 and 7 induce endochondral bone formation, whereas a related molecule BMP 12/GDF7 induces connective tissue similar to tendon. Similarly, BMP4 can induce cell death in the hindbrain neural crest, while the related protein dorsalin does not.

Since different BMP family members can induce different fates, then BMP antagonists that have specificity in blocking subsets of BMPs could change the balance of BMPs that are presented to a cell, thus altering cell fate. In view of the importance of relative BMP expression in human health and disease, regulators of cellular function and BMP function in particular; such as noggin and cerberus, provide valuable reagents with a host of clinical and biotechndlogical applications.

The present invention relates to a new family of regulators of cellular function; in particular, we have identified a new dorsalizing factor Gremlin. Gremlin's activities are similar to those of Noggin and Chordin, however, it has no sequence similarity to them, and it is not expressed during gastrulation. Instead, zygotic Gremlin expression begins in the migrating neural crest, highlighting a potential role for organizer-like activities in the development of this cell lineage. Furthermore, we have identified a structurally and functionally-related family of proteins that includes Gremlin, the head-inducing factor Cerberus and the tumor suppressor DAN (Ozaki and Sakiyama, 1993; Bouwmeester et al., 1996). We have named this family the DAN family for the first member identified. Cerberus is expressed in the anterior endomesoderm of the gastrula organizer and has been proposed to participate in head induction (Bouwmeester et al., 1996). DAN was isolated as a putative zinc-finger protein 4downregulated in transformed cells and was subsequently shown to have tumor suppressor activity (Ozaki and Sakiyama, 1993; Ozaki and Sakiyama, 1994). Similarly, the rat homolog of Gremlin, drm, has also been proposed to have a role in controlling cell growth and differentiation (Topol et al., 1997). We demonstrate that all members of the DAN family act as BMP antagonists, while Cerberus alone blocks the activity of Activin and Nodal-like activities. We also show that DAN-family members are secreted proteins that bind BMP-2. Together, our data reveal that individual DAN-family members block the activity of specific TGF-β ligands by binding them and preventing them from interacting with their cell surface receptors.

RELEVANT LITERATURE

Altschul, S. F., et al. (1990) J Mol Biol 215, 403–10.
Badley, J. E., et al. (1988) Biotechniques 6, 114–6.
Baker, J. C., and Harland, R. M. (1996) Genes & Development 10, 1880–1889.
Belo, J. A., et al. (1997) Mechanisms Of Development 68, 45–57.
Bolce, M. E., et al. (1992) Development 115, 681–8.
Bouwmeester, T., et al. (1996) Nature 382, 595–601.
Clement, J. H., et al. (1995)Mech Dev 52, 357–70.
Collazo, A., Bronner-Fraser, M., and Fraser, S. E. (1993) Development 118, 363–76.
Dale, L., et al. (1992) Development 115, 573–85.
Estevez, M., et al. (1993) Nature 365, 644–9.
Fainsod, A et al. (1994) EMBO J. 13, 5015–5025.
Gimlich, R. L., and Gerhart, J. C. (1984) Developmental Biology 104, 117–130.
Harland, R. M., and Gerhart, J. C. (1997) In Ann reviews Cell and Dev Biol, pp. 611–667.
Hemmati-Brivanlou, A., et al. (1994) Cell 77, 283–295.
Hemmati-Brivanlou, A., and Thomsen, G. H. (1995)-4. Dev Genet 17, 78–89.
Hogan, B. L., et al. (1994) Dev Suppl, 53–60.
Holley, S. A., et al. (1996) Cell 86, 607–17.
Jones, C. M., et al. (1995) Development 121, 3651–62.
Jones, C. M., et al. (1992) Development 115, 639–47.
Joseph, E. M., and Melton, D. A. (1997) Dev Biol 184, 367–72.
Kao, K. R., and Elinson, R. P. (1988) Devi Biol. 127, 64–77.
Kintner, C. R., and Brockes, J. P. (1984) Nature 308, 67–69.
Kintner, C. R., and Melton, D. A. (1987) Development 99, 311–25.
Krotoski, D. M., et al. (1988) Dev Biol 127, 119–32.
Lamb, T. M., et al. (1993) Science 262, 713–8.
Lemaire, P., Garrett, N., and Gurdon, J. B. (1995) Cell 81, 85–94.

Lennon, G., et al. (1996) Genomics 33, 151–2.
Ozaki, T., and Sakiyama, S. (1993) Proc Natl Acad Sci U S A 90, 2593–7.
Ozaki, T., and Sakiyama, S. (1994) Cancer Res 54, 646–8.
Peng, H. B. (1991) In Methods in Cell Biology 36, B.K. Kay, H.B. Peng, eds., pp. 661–662.
Piccolo, S., Sasai, Y., Lu, B., and De Robertis, E. M. (1996) Cell 86, 589–98.
Ren, P., et al. (1996) Science 274, 1389–91.
Sadaghiani, B., and Thiebaud, C. H. (1987) Dev Biol 124, 91–110.
Sasai, Y., and De Robertis, E. M. (1997) Dev Biol 182, 5–20.
Sasai, Y., et al. (1995) Nature 376, 333–336.
Sasai, Y., et al. (1994) Cell 79, 779–790.
Savage, C., et al. (1996) Proc Natl Acad Sci U S A 93, 790–4.
Schmidt, J. E., et al. (1995) Developmental Biology 169, 37–50.
Smith, J. C., et al. (1990) Nature 345, 729–31.
Smith, J. C., et al. (1991) Cell 67, 79–87.
Smith, W. C., and Harland, R. M. (1992) Cell 70, 829–40.
Smith, W. C., and Harland, R. M. (1991) Cell 67, 753–765.
Smith, W. C., Knecht, A. K., Wu, M., and Harland, R. M. (1993) Nature 361, 547–9.
Smith, W. C., McKendry, R., Ribisi, S., and Harland, R. M. (1995) Cell 82, 37–46.
Thies, R. S., et al. (1992) Endocrinology 130, 1318–24.
Thomas, P., et al. (1997) Cold Spring Harbor Symposia on Quantitative Biology 62.
Thomsen, G., et al. (1990) Cell 63, 485–93.
Thomsen, G. H., and Melton, D. A. (1993) Cell 74, 433–441.
Topol, L. Z., et al. (1997) Molecular and Cellular Biology 17, 4801–4810.
Turner, D. L., and Weintraub, H. (1994) Genes Devel. 8, 1434–1447.
Varlet, I., Collignon, J., and Robertson, E. J. (1997) Development 124, 1033–44.
Vize, P. D., Jones, E. A., and Pfister, R. (1995) Dev Biol 171, 531–40.
Wieser, R., Wrana, J. L., and Massague, J. (1995) Embo J 14, 2199–208.
Wilson, P. A., and Hemmati-Brivanlou, A. (1995) Nature 376, 331–3.
Wilson, P. A., and Melton, D. A. (1994) Curr Biol 4, 676–86.
Zimmerman, L. B., et al. (1996) Cell 86, 599–606.

SUMMARY OF THE INVENTION

The invention provides methods and compositions relating to DAN (Differential-screening-selected gene Aberrative in Neuroblastoma) and gremlin proteins and related nucleic acids. Included are natural DAN and gremlin homologs from different species and DAN and gremlin proteins comprising a DAN or gremlin domain and having DAN or gremlin-specific activity, particularly the ability to antagonize a bone morphogenic protein such as BMP2 or BMP4. The proteins may be produced recombinantly from transformed host cells with the subject nucleic acids. The invention provides isolated hybridization probes and primers capable of specifically hybridizing with the disclosed genes, specific binding agents such as specific antibodies, and methods of making and using the subject compositions in diagnosis (e.g. genetic hybridization screens for gremlin transcripts), therapy (e.g. gene therapy to modulate gremlin gene expression) and in the biopharmaceutical industry (e.g. reagents for screening chemical libraries for lead pharmacological agents).

Preferred applications of the subject DAN and gremlin proteins include modifying the physiology of a cell comprising an extracellular surface by contacting the cell or medium surrounding the cell with an exogenous DAN or gremlin protein under conditions whereby the added protein specifically interacts with a component of the medium and/or the extracellular surface to effect a change in the physiology of the cell. Also preferred are methods for screening for biologically active agents, which methods involve incubating a DAN or gremlin protein in the presence of an extracellular DAN or gremlin protein-specific binding target and a candidate agent, under conditions whereby, but for the presence of the agent, the protein specifically binds the binding target at a reference affinity; detecting the binding affinity of the protein to the binding target to determine an agent-biased affinity, wherein a difference between the agent-biased affinity and the reference affinity indicates that the agent modulates the binding of the protein to the binding target.

BRIEF DESCRIPTION OF THE FIGURE

FIG. 1. FIG. 1(A) shows a sequence alignment of Gremlin sequences identified in Xenopus(x)(SEQ ID NO:04), chick (c)(SEQ ID NO:06), mouse(m)(SEQ ID NO:09), and human (h)(SEQ ID NO:02), showing that they are >80% identical. The predicted signal sequence is in bold. A single N-linked glycosylation site is underlined. The nine cysteines in the carboxy-terminal domain are marked with asterisks. FIG. 1(B) shows a sequence alignment of the cysteine-rich domain shared by Xenopus Gremlin (xGremlin)(SEQ ID NO:04), Xenopus Cerberus (xCerberus)(SEQ ID NO:12), mouse DAN (mDAN)(SEQ ID NO:10), Xenopus DAN (xDAN)(SEQ ID NO:11), and C. elegans Gremlin-related-1 (ceGR-1)(SEQ ID NO:13). Conserved cysteines are marked with asterisks.

DETAILED DESCRIPTION OF THE INVENTION

The nucleotide sequence of a natural cDNA encoding human, xenopus and chick gremlin polypeptides are shown as SEQ ID NOS:1, 3, and 5, respectively, and the corresponding full conceptual translates are shown as SEQ ID NOS:2, 4 and 6. The nucleotide sequence of a natural cDNA encoding a human DAN polypeptide is shown as SEQ ID NO:7, and the corresponding full conceptual translate is shown as SEQ ID NO:8. The gremlin and DAN polypeptides of the invention include one or more functional domains comprising at least 8, preferably at least 12, more preferably at least 18, more preferably at least 36 contiguous residues of the recited SEQ ID NOS and have an assay-discernable DAN or gremlin-specific activity, functionally distinct from each other and from cerberus and noggin homologs. For example, gremlin specific polynucleotides and polypeptides having human gremlin-specific sequences are readily discernable from alignments of the sequences. Preferred gremlin polypeptides have one or more human gremlin-specific activities, such as cell surface receptor binding and/or binding inhibitory activity and gremlin-specific immunogenicity and/or antigenicity. In a particular embodiment, the DAN or gremlin polypeptides retain the nine conserved cysteine residues, and preferably all contiguous sequence contained within the native nine conserved cysteine residues of the family as discernable by alignment (FIGS. 1A, 1B).

DAN or gremlin-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of a DAN or gremlin polypeptide with a binding target is evaluated. The binding target maybe a natural extracellular binding target such as a TGFβ protein, a morphogenic protein, preferably a bone morphogenic protein such as BMP2 or BMP4; or non-natural binding target such as a specific immune protein such as an antibody, or a DAN or gremlin specific agent such as those identified in screening assays such as described below. DAN or gremlin-binding specificity may be assayed by binding equilibrium constants (usually at least about $10^7 M^{-1}$, preferably at least about $10^8 M^{-1}$ more preferably at least about $10^9 M^{-1}$), by growth cone collapse assays, by the ability to elicit gremlin specific antibody in a heterologous host (e.g a rodent or rabbit), etc.

For example, deletion mutagenesis is used to define functional DAN and gremlin domains which specifically bind BMPs in in vitro and cell-based assays described below.

TABLE 1

Exemplary DAN and gremlin deletion mutants defining functional domains.

| Mutant | Sequence | BMP Binding |
|---|---|---|
| GΔN1 | SEQ ID NO:2, residues 2–184 | + |
| GΔN2 | SEQ ID NO:2, residues 12–184 | + |
| GΔN3 | SEQ ID NO:2, residues 24–184 | + |
| GΔN4 | SEQ ID NO:2, residues 48–184 | + |
| GΔN5 | SEQ ID NO:2, residues 64–184 | + |
| GΔC1 | SEQ ID NO:2, residues 1–183 | + |
| GΔC2 | SEQ ID NO:2, residues 1–182 | + |
| GΔC3 | SEQ ID NO:2, residues 1–181 | + |
| GΔC4 | SEQ ID NO:2, residues 1–180 | + |
| GΔC5 | SEQ ID NO:2, residues 1–179 | + |
| GΔNC1 | SEQ ID NO:2, residues 21–181 | + |
| GΔNC2 | SEQ ID NO:2, residues 34–182 | + |
| GΔNC3 | SEQ ID NO:2, residues 57–183 | + |
| GΔNC4 | SEQ ID NO:2, residues 13–183 | + |
| GΔNC5 | SEQ ID NO:2, residues 45–181 | + |
| DΔN1 | SBQ ID NO:8, residues 3–181 | + |
| DΔN2 | SEQ ID NO:8, residues 8–181 | + |
| DΔN3 | SEQ ID NO:8, residues 18–181 | + |
| DΔN4 | SEQ ID NO:8, residues 23–181 | + |
| DΔN5 | SEQ ID NO:8, residues 28–181 | + |
| DΔC1 | SEQ ID NO:8, residues 1–180 | + |
| DΔC2 | SEQ ID NO:8, residues 1–179 | + |
| DΔC3 | SEQ ID NO:8, residues 1–178 | + |
| DΔC4 | SEQ ID NO:8, residues 1–177 | + |
| DΔC5 | SEQ ID NO:8, residues 1–176 | + |
| DΔNC1 | SEQ ID NO:8, residues 3–180 | + |
| DΔNC2 | SEQ ID NO:8, residues 2–177 | + |
| DΔNC3 | SEQ ID NO:8, residues 7–179 | + |
| DΔNC4 | SEQ ID NO:8, residues 16–180 | + |
| DΔNC5 | SEQ ID NO:8, residues 21–178 | + |

In a particular embodiment, the subject domains provide DAN or gremlin-specific antigens and/or immunogens, especially when coupled to carrier proteins. For example, peptides corresponding to gremlin- and human gremlin-specific domains are covalently coupled to keyhole limpet antigen (KLH) and the conjugate is emulsified in Freunds complete adjuvant. Laboratory rabbits are immunized according to conventional protocol and bled. The presence of DAN or gremlin-specific antibodies is assayed by solid phase immunosorbant assays using immobilized DAN or gremlin polypeptides, see, e.g. Table 2.

TABLE 2

Immunogenic human gremlin polypeptides eliciting gremlin-specific rabbit polyclonal antibody: gremlin polypeptide-KLH conjugates immunized per protocol described above.

| Gremlin Polypeptide Sequence | Immunogenicity |
|---|---|
| SEQ ID NO:2, residues 1–8 | +++ |
| SEQ ID NO:2, residues 2–11 | +++ |
| SEQ ID NO:2, residues 12–21 | +++ |
| SEQ ID NO:2, residues 15–23 | +++ |
| SEQ ID NO:2, residues 22–30 | +++ |
| SEQ ID NO:2, residues 32–39 | +++ |
| SEQ ID NO:2, residues 42–51 | +++ |
| SEQ ID NO:2, residues 45–52 | +++ |
| SEQ ID NO:2, residues 52–65 | +++ |
| SEQ ID NO:2, residues 68–79 | +++ |
| SEQ ID NO:2, residues 70–80 | +++ |
| SEQ ID NO:2, residues 75–82 | +++ |
| SEQ ID NO:2, residues 86–92 | +++ |
| SEQ ID NO:2, residues 92–98 | +++ |
| SEQ ID NO:2, residues 95–103 | +++ |
| SEQ ID NO:2, residues 99–108 | +++ |
| SEQ ID NO:2, residues 102–112 | +++ |
| SEQ ID NO:2, residues 109–115 | +++ |
| SEQ ID NO:2, residues 116–123 | +++ |
| SEQ ID NO:2, residues 119–126 | +++ |
| SEQ ID NO:2, residues 222–130 | +++ |
| SEQ ID NO:2, residues 124–135 | +++ |
| SEQ ID NO:2, residues 127–140 | +++ |
| SEQ ID NO:2, residues 138–147 | +++ |
| SEQ ID NO:2, residues 145–155 | +++ |
| SEQ ID NO:2, residues 149–151 | +++ |
| SEQ ID NO:2, residues 157–165 | +++ |
| SEQ ID NO:2, residues 160–168 | +++ |
| SEQ ID NO:2, residues 167–181 | +++ |

The claimed gremlin polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The gremlin polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art. An exemplary method for isolating natural DAN and gremlin proteins involves expressing a cDNA library (e.g. derived from xenopus ovarian cells) and assaying expression products for embryonic axis formation. This method and other suitable bioassays amenable to detecting DAN and gremlin proteins have been described by Lemaire P; et al. (supra); Smith, W. C., and Harland, R. M. (1992 and 1991, supra); Piccolo, S., et al. (1996, supra); and Zimmerman, L. B., et al. (1996, supra).

The invention provides binding agents specific to DAN or gremlin polypeptides, preferably the claimed human gremlin polypeptides, including agonists, antagonists, natural cell surface receptor binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins. Novel DAN or gremlin-specific binding agents include DAN or gremlin-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural binding agents such as Gremlin cell surface receptors, non-natural intracellular binding agents identified in screens of chemical libraries such as described below, etc. Agents of particular interest modulate DAN or gremlin function, e.g. gremlin-modulatable cellular physiology.

The subject proteins find a wide variety of uses including use as immunogens, targets in screening assays, bioactive reagents for modulating cell growth, differentiation and/or function, etc. For example, the invention provides methods for modifying the physiology of a cell comprising an extracellular surface by contacting the cell or medium surrounding the cell with an exogenous DAN or gremlin protein under conditions whereby the added protein specifically interacts with a component of the medium and/or the extracellular surface to effect a change in the physiology of the cell. According to these methods, the extracellular surface includes plasma membrane-associated receptors; the exogenous DAN or gremlin refers to a protein not made by the cell or, if so, expressed at non natural levels, times or physiologic locales; and suitable media include in vitro culture media and physiological fluids such as blood, synovial fluid, etc. Effective administrations of subject proteins can be used to reduce undesirable (e.g. ectopic) bone formation, inhibit the growth of cells that require a morphogenic protein (e.g. BMP-dependent neuroblastomas and gliomas), alter morphogen-dependent cell fate/differentiation in culture, such as with cells for transplantation or infusion, etc. The proteins may be may be introduced, expressed, or repressed in specific populations of cells by any convenient way such as microinjection, promoter-specific expression of recombinant enzyme, targeted delivery of lipid vesicles, etc.

In one embodiment, the invention provides methods for modulating cell function comprising the step of modulating DAN or gremlin activity, e.g. by contacting the cell with a DAN or gremlin polypeptide. In preferred embodiments, the modulator effects gremlin or DAN mediated decrease in resident BMP activity. The target cell may reside in culture or in situ, i.e. within the natural host. The modulator may be provided in any convenient way, including by (i) intracellular expression from a recombinant nucleic acid or (ii) exogenous contacting of the cell. For many in situ applications, the compositions are added to a retained physiological fluid such as blood or synovial fluid. DAN and gremlin polypeptides or polypeptide modulators may also be amenable to direct injection or infusion, topical, intratracheal/nasal administration e.g. through aerosol, intraocularly, or within/on implants e.g. fibers e.g. collagen, osmotic pumps, grafts comprising appropriately transformed cells, etc. See e.g. Tracy M A (1998) Biotechnol Prog 14(1):108–115; Putney S D, Burke P A (1998) Nat Biotechnol 16(2):153–157 for encapsulation delivery methods. Generally, the amount administered will be empirically determined, typically in the range of about 10 to 1000 $\mu$g/kg of the recipient and the concentration will generally be in the range of about 50 to 500 $\mu$g/ml in the dose administered, see e.g. Lucidi P, et al. (1998) J Clin Endocrinol Metab 83(2):353–357; Houdijk E C, et al. (1997) Acta Paediatr 86(12):1301–1307 for suitable methods of administration.

Other additives may be included, such as stabilizers, bactericides, etc. will be present in conventional amounts. For diagnostic uses, the modulators or other gremlin binding agents are frequently labeled, such as with fluorescent, radioactive, chemiluminescent, or other easily detectable molecules, either conjugated directly to the binding agent or conjugated to a probe specific for the binding agent.

For example, rats implanted with BMP-4 collagen matrices are used to demonstrate in vivo efficacy of gremlin and DAN polypeptides. In these experiments, rats are implanted with BMP-4 collagen matrices substantially as described in Wozney et al. (1988) Science 242:1528–1534 and treated with three gremlin polypeptides (SEQ ID NO:2, SEQ ID NO2, residues 24–182, and SEQ ID NO:2, residues 54–180 or two DAN polypeptides (SEQ ID NO:8, SEQ ID NO:8, residues 12–181. All five treatment groups demonstrate significant reductions in ectopic (matrix) bone formation. Gremlin and DAN polypeptides are also demonstrated to antagonize recombinant human BMP-2-mediated bone formation in rabbits, essentially as described in Zegzula HD, et al. (1997) J Bone Joint Surg Am 79(12): 1778–1790. Briefly, A unilateral segmental defect, twenty millimeters long, is created in the radius in ninety-six skeletally )nature New Zealand White rabbits. Forty-eight rabbits are evaluated at four weeks and forty-eight, at eight weeks. Eight groups are studied at each time-period. The defect is filled with a porous poly(DL-lactic acid) implant containing zero, 17, 35, or 70 micrograms of rhBMP-2 with and without either zero, 20, 100, or 500 micrograms gremlin polypeptide (SEQ ID NO:2, residues 24–184) or 100 or 250 micrograms DAN polypeptide (SEQ ID NO:8, residues 12–181). Radiographs of the defects are made every two weeks. The percentage of the total area of the defect that is radiopaque is determined with use of computerized radiomorphometry, and this percentage used as a quantitative measure of the extent of new-bone formation in the defect. Time and dose-dependent responses to rhBMP-2 are found for as long as four weeks; thereafter, the effects of seventeen, thirty-five, and seventy micrograms of rhBMP-2 are independent of dose and time ($p<or=0.05$). The defects treated with either thirty-five or seventy micrograms of rhBMP-2 have a significantly greater ($p<or=0.05$) area of radiopacity than the defects treated with either zero or seventeen micrograms of rhBMP-2. No significant difference is found between the defects treated with thirty-five or seventy micrograms of rhBMP-2 and the defects filled with an autogenous graft. All defects concomitantly treated with all three doses of gremlin and both doses of DAN reveal significantly less ($p<or=0.05$) area of radiopacity than the corresponding rhBMP-2 only treated groups. The inhibition of BMP-2 mediated bone formation is confirmed by histological and histomorphometric examinations.

The amino acid sequences of the disclosed DAN and gremlin polypeptides are used to back-translate gremlin polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural gremlin-encoding nucleic acid sequences ("GCG" software, Genetics Computer Group, Inc, Madison Wis.). DAN and gremlin-encoding nucleic acids used in DAN and gremlin-expression vectors and incorporated into recombinant host cells, e.g. for expression and screening transgenic animals, e.g. for functional studies such as the efficacy of candidate drugs for disease associated with gremlin-modulated cell function, etc.

The invention also provides nucleic acid hybridization probes and replication/amplification primers having a DAN or gremlin cDNA specific sequence comprising a strand of least one of SEQ ID NO:1 or 7, or at least 18, preferably at least 36, more preferably at least 72 contiguous nucleotides of SEQ ID NO:1 or 7 and sufficient to specifically hybridize with a second nucleic acid comprising the complementary strand of the corresponding SEQ ID NO:1 or 7. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising; 50% formamide in 5×SSPE buffer at a temperature of 42° C. and remaining bound when subject to washing at 42° C. with 0.2×SSPE buffer at 42° C.

TABLE 3

Exemplary gremlin nucleic acids which hybridize with a strand of SEQ ID NO: 1 under Conditions I and/or II.

| gremlin Nucleic Acids | Hybridization |
|---|---|
| SEQ ID NO:1, nucleotides 1–36 | + |
| SEQ ID NO:1, nucleotides 68–98 | + |
| SEQ ID NO:1, nucleotides 95–130 | + |
| SEQ ID NO:1, nucleotides 175–220 | + |
| SEQ ID NO:1, nucleotides 261–299 | + |
| SEQ ID NO:1, nucleotides 274–310 | + |
| SBQ ID NO:1, nucleotides 331–369 | + |
| SEQ ID NO:1, nucleotides 430–470 | + |
| SEQ ID NO:1, nucleotides 584–616 | + |

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, or requisite fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of gremlin genes and gene transcripts and in detecting or amplifying nucleic acids encoding additional gremlin homologs and structural analogs. In diagnosis, gremlin hybridization probes find use in identifying wild-type and mutant gremlin alleles in clinical and laboratory samples. Mutant alleles are used to generate allele-specific oligonucleotide (ASO) probes for high-throughput clinical diagnoses. DAN and gremlin nucleic acids are also used to modulate cellular expression or intracellular concentration or availability of active DAN or gremlin. DAN and gremlin inhibitory nucleic acids are typically antisense: single-stranded sequences comprising complements of the disclosed natural gremlin coding sequences. Antisense modulation of the expression of a given DAN or gremlin protein may employ antisense nucleic acids operably linked to gene regulatory sequences. Cell are transfected with a vector comprising a DAN or gremlin sequence with a promoter sequence oriented such that transcription of the gene yields an antisense transcript capable of binding to endogenous DAN/gremlin encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given DAN or gremlin protein may be administered to the target cell, in or temporarily isolated from a host, at a concentration that results in a substantial reduction in expression of the targeted protein. An enhancement in DAN or gremlin expression is effected by introducing into the targeted cell type DAN or gremlin nucleic acids which increase the functional expression of the corresponding gene products. Such nucleic acids may be DAN or gremlin expression vectors, vectors which upregulate the functional expression of an endogenous allele, or replacement vectors for targeted correction of mutant alleles. Techniques for introducing the nucleic acids into viable cells are known in the art and include retroviral-based transfection, viral coat protein-liposome mediated transfection, etc.

The invention provides efficient methods of identifying agents, compounds or lead compounds for agents active at the level of a gremlin modulatable cellular function. Generally, these screening methods involve assaying for compounds which modulate gremlin interaction with a natural gremlin binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including a DAN or gremlin protein, which may be part of a fusion product with another peptide or polypeptide, e.g. a tag for detection or anchoring, etc. The assay mixtures comprise a natural DAN/gremlin binding target, e.g. a TGFβ protein such as a BMP. While native binding targets may be used, it is frequently preferred to use portions thereof so long as the portion provides binding affinity and avidity to the subject DAN/gremlin conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents such as salts, buffers, neutral proteins, e.g. albumin, detergents, protease inhibitors, nuclease inhibitors, antimicrobial agents, etc. may also be included. The mixture components can be added in any order that provides for the requisite bindings and incubations may be performed at any temperature which facilitates optimal binding. The mixture is incubated under conditions whereby, but for the presence of the candidate pharmacological agent, the DAN or gremlin specifically binds the cellular binding target, portion or analog with a reference binding affinity. Incubation periods are chosen for optimal binding but also minimized to facilitate rapid, high-throughput screening. After incubation, the agent-biased binding between the DAN or gremlin and one or more binding targets is detected by any convenient way. For cell-free binding type assays, a separation step is often used to separate bound from unbound components. Separation may be effected by precipitation, immobilization, etc., followed by washing by, for examples, membrane filtration, gel chromatography. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components, e.g. through optical or electron density, radiative emissions, nonradiative energy transfers, etc. or indirectly detected with antibody conjugates, etc. A difference in the binding affinity of the DAN/gremlin protein to the target in the absence of the agent as compared with the binding affinity in the presence of the agent indicates that the agent modulates the binding of the DAN/gremlin protein to the corresponding binding target. A difference, as used herein, is statistically significant and preferably represents at least a 50%, more preferably at least a 90% difference.

The following examples are offered by way of illustration and not by way of limitation.

EXAMPLES

Expression Cloning of Gremlin. To identify new axial patterning activities in the Xenopus embyro, we screened for maternally-supplied activities whose ventral expression induced a secondary axis in otherwise normal embryos (Lemaire et al., 1995). 1 ng of synthetic MRNA from each pool of a Xenopus ovary cDNA library was injected into a ventral blastomere of a 4-cell embryo. Injected embryos were subsequently screened at the tailbud stage for presence of a secondary axis. Using this procedure, two pools with axis-inducing activity Mere identified. One pool contained Activin-βB (Thomsen et al., 1990), and was eliminated from further consideration. Fractionation of the second pool identified a single clone with potent activity. mRNA doses as low as 50 pg induced a secondary axis or hyperdorsalization in 93% of ventrally-injected embryos. In contrast to the complete secondary axes that can be induced by activation of the Wnt signaling pathway, higher doses of this clone induced rostral structures such as eyes in fewer than 5% of injected embryos. The sequence of the 1.8 kb cDNA encodes a predicted protein that we have named Gremlin.

To characterize Gremlin's axis-inducing activity, we traced the fate of Gremlin-expressing cells in twinned embryos. 50 pg of Gremlin mRNA and 80 pg of mRNA encoding a β-Galaclosidase lineage tracer were injected equatorially into ventral blastomere of 4-cell embryos. At tailbud stage, embryos were fixed and stained with X-Gal. Not all the cells in the secondary axis were stained, indicating that Gremlin-expressing cells are able to recruit neighboring cells into the induced axis. While Gremlin induced secondary axes efficiently when injected into the marginal zone, it did not when injected into a ventral-vegetal blastomere. Thus, despite its maternal origin, Gremlin is not the vegetally-localized dorsalizing signal emanating from the Nieuwkoop center (Gimlich and Gerhart, 1984; Smith and Harland, 1991).

The composition and patterning of Gremlin-induced secondary axes was examined by immunostaining injected embryos with monoclonal antibodies that detect muscle, notochord, or neural tissue. We found that Gremlin-induced secondary axes frequently contain all three tissue types, and that each tissue is organized in a relatively normal fashion. Muscle staining is organized in regularly repeated somitic segments, while neural and notochord tissue stain in patterns similar to those found in the primary axis. Thus, the composition and pattern of Gremlin-induced axes resembles that of normal axes.

Gremlin is Expressed in the Neural Crest. We used in situ hybridization to determine Gremlin's temporal and spatial expression patterns (Lamb et al., 1993). Maternal Gremlin transcripts are present, but not localized in early-stage oocytes, and they are undetectable in mature oocytes and early stage embryos (not shown). Despite its axial patterning activities, Gremlin is not expressed during gastrulation. Instead, zygotic Gremlin expression begins at tailbud stages, where it is largely correlated with neural crest lineages. At stage 27, Gremlin staining appears in the pronephric duct, with additional faint staining in the trunk and tail bud. Staining in the pronephric duct may identify neural crest cells known to contribute to this structure (Collazo et al., 1993). In stage 30–40 embryos, Gremlin expression extends rostrally and caudaily to include neural crest cells at all axial levels. In the head, staining is present in the mandibular segment of the neural crest (Sadaghiani and Thiebaud, 1987). Caudally, staining illuminates the dorsal migration of neural crest cells into the fin, as well as the chevron-shaped pathways of their ventral migration (Sadaghiani and Thiebaud, 1987; Krotoski et al., 1988; Collazo et al., 1993). In addition, expression continues in the pronephric duct as it extends caudaily (Vize et al., 1995). These observations were confirmed by examination of transverse sections. Taken together, Gremlin's expression pattern indicates role in neural crest induction and patterning.

Gremlin Identifies a Family of Secreted Proteins With Axial Patterning Activity. The DNA sequence of the 1.8 kb Gremlin cDNA predicts a 182 amino acid protein with an N-terminal hydrophobic sequence, a site for N-linked glycosylation, and a C-terminal cysteine-rich domain (FIG. 1A). For comparative studies, we identified chick, mouse, and human Gremlin homologs, and found that they share over 80% amino acid identity with Xenopus Gremlin (FIG. 1A). Recently, drm, a rat Gremlin homolog with over 80% similarity to the Gremlin family was identified as a cDNA downregulated in v-mos transformed cells (Topol et al., 1997).

BLAST searches revealed that Gremlin belongs to a new family of proteins that includes the previously-identified proteins, Cerberus and DAN (Topol et al., 1997)(FIG. 1B). Cerberus is a secreted factor expressed in the Xenopus gastrula that acts as a potent inducer of head structures (Bouwmeester et al., 1996; Belo et al., 1997). DAN encodes a tumor suppressor originally identified in rat as a down-regulated transcript in transformed cells (Ozaki and Sakiyama, 1993). We also isolated a partial cDNA encoding a nematode Gremlin homolog that has been designated C. elegans Gremlin-Related-1 (ceGR-1). We name this family the DAN family for the first member to be reported. Sequence alignments show that each protein has a domain with the consensus sequence $CX_6QX_6CX_6NX_2CXGXCXSX_3PX_{(8-13)}CX_2CXPX_8TLXCX_{(15-18)}CXC$ (FIG. 1B). Outside this domain, DAN-family members show little similarity.

The protein sequences of Gremlin, Cerberus, and DAN all contain a likely signal sequence. However, while Cerberus has been reported as a secreted protein, DAN was initially identified as a putative zinc-finger protein. To determine whether all DAN-family members are secreted, synthetic mRNA encoding Gremlin, DAN, or Cerberus was injected into oocyteF that were then cultured in the presence of $^{35}$S methionine. We found that supernatants of Gremlin and DAN-injected oocytes contained proteins of approximately 28 kd and 27 kd, respectively. Cerberus-injected oocytes secreted a heterogeneous product centered around 40 kd. Thus, all DAN-family members are secreted proteins. The predicted molecular weights for Gremlin (25 kd), DAN (19 kd), and Cerberus (31 kd) are lower than those observed, indicating that all three proteins undergo post-translational modification. Consistently, Gremlin, Cerberus, and DAN all have sites for N-linked glycosylation (Ozaki and Sakiyama, 1993; Bouwmeester et al., 1996).

DAN Has Dorsalizing Activity in Xenopus Embryos. While axial patterning activities have been shown for Gremlin and Cerberus, none have been shown for DAN. However, the similarity between the three proteins led us to test DAN for embryonic patterning activity. As a preliminary assay, we injected 100 pg synthetic DAN mRNA into the marginal zone of both ventral blastomeres of 4-cell embryos. At this dose, DAN-injected embryos were mildly hyperdorsalized (DAI 6-7) (Kao and Elinson, 1988) with slightly enlarged heads, bloated trunks, and a reduction of tail structures. Occasionally, injected embryos had a secondary axis (less than 10%). Immunostaining of DAN-injected embryos using the muscle specific antibody 12/101 reveals that muscle is present, but that it is poorly organized. Xenopus DAN had similar activity. DAN's activity in embryos and its ability to dorsalize ventral mesoderm and neuralize ectoderm (described below) establishes that all DAN-family members have axial patterning activity.

DAN-Family Members Act Like BMP Antagonists in Embryonic Explants. To further examine the biological activities of DAN-family members, we tested their ability to pattern mesoderm using the ventral marginal zone (VMZ) assay (Smith et al., 1993). Consistent with their effects when expressed ventrally in embryos, expression of 100 pg DAN or Gremlin mRNA induced the dorsal mesodermal marker cardiac muscle actin (M. actin) in VMZ explants. As previously reported, the same dose of Cerberus mRNA failed to induce M. actin (Bouwmeester et al., 1996). Since Cerberus failure to dorsalize the VMZ is probably due to its ability to provide an early block to mesoderm induction (described below), we repeated the VMZ assay with a Cerberus DNA construct that is not transcriptionally active until blastula stages. When its expression was delayed, Cerberus also induced M. actin. In Xenopus, an accumulated body of evidence has shown that dorsalization of mesoderm can result from blocking vertralizing signals provided by members of the BMP family (Reviewed in Harland and Gerhart, 1997). In light of these observations, the dorsalizing activity of Cerberus, DAN, and Gremlin indicates that they act by antagonizing BMP signals.

We also tested the activities of DAN-family members in animal cap explants. These experiments show that Gremlin, Cerberus, and DAN induce neural tissue from animal cap ectoderm. Injection of 100 pg Gremlin, 1 ng Cerberus, or 10 ng DAN into the animal pole of a 1-cell embryo induced neural differentiation in explants, as evidenced by expression of the pan-neural maker NCAM (Kintner and Melton, 1987; Bouwmeester et al., 1996). The absence of M. actin induction indicates that neuralization occurred directly, without a mesodermal intermediary.

In Xeropus, organizer-specific neuralizing signals act by antagonizing signaling by BMPs that normally cause ectoderm to adopt an epidermal fate (Reviewed in Harland and Gerhart, 19971 Sasai and De Robertis, 1997). To test whether DAN-family members neuralize through a similar mechanism, we co-expressed each one with an activated form of a type I BMP-4 receptor. ALK-3(Q233D) contains a Q to D mutation at position 233 that activates the receptor kinase, leading to constitutive signaling in the BMP signal transduction pathway (Wieser et al., 1995; Holley et al., 1996). We found that expression of ALK-3(Q233D) blocks neural induction by Gremlin, Cerberus, or DAN, indicating that they block BMP signaling upstream of the receptor.

Cerberus expression in animal cap explants also induced modest levels of the pan-endodermal marker endodermin (Edd), and the cardiac marker Nkx 2.5 (Bouwmeester et al., 1996). We find that Gremlin and DAN share these activities. 100 pg of Cerberus, Gremlin, or DAN mRNA induced Edd and Nkx 2.5 at low to moderate levels. We also found that induction of these markers occurs in the presence or absence of ALK-3(Q233D), indicating that induction of these genes is normally not suppressed by BMP signaling through ALK-3. These findings indicate that in addition to BMP antagonizing activities, DAN-family members can block the activities of additional TGF-β signals.

Gremlin Blocks the Activity of Purified BMP-2. Gremlin's dorsalizing and neuralizing activities provide a strong indication that it acts by antagonizing signaling by members of the BMP family. As a more direct test of Gremlin's activity, we examined its ability to antagonize the activity of purified BMP-2 in a cytokine assay. The murine bone marrow stromal cell line W-20-17 provides a direct, quantitative bioassay for BMP activity by induction of alkaline phosphataee in response to BMP treatment (Thies et al., 1992). Preincubation of purified BMP-2 with a Gremlin COS supernatant at a final concentration of ~83 nM Gremlin completely blocked BMP-2 activity at doses from 78 pM to 5 nM. At ~21 nM Gremlin, BMP-2 activity was reduced, but not eliminated. In contrast, a mock-transfected COS supernatant had no effect. Similar results were obtained with BMP-4. Thus, like Noggin and Chordin, Gremlin blocks BMP activity in multiple assays.

DAN-Family Members Bind BMP-2. Biochemical studies of the BMP antagonists Noggin and Chordin have shown that they bind BMP-4 with high affinity, preventing it from interacting with its cell surface receptors (Piccolo et al., 1996; Zimmerman et al., 1996). To test whether DAN-family members antagonize BMP signaling through a similar mechanism, we examined their ability to associate with BMP-2, which has activities virtually indistinguishable from those of BMP-4. Gremlin, DAN, or Cerberus COS-conditioned supernatants were incubated with anti BMP-2 protein G sepharose beads in the presence or absence of 1 μg BMP-2. After binding, beads were processed and analyzed by Western blot. We found that Cerberus, DAN, and Gremlin are precipitated by anti-BMP-2 beads in a BMP-2-dependent fashion. Reciprocal binding experiments confirm that DAN-family members associate with BMP-2. When Cerberus was precipitated using an anti-Cer polyclonal antibody, BMP-2 coprecipitated. A similar result was obtained when DAN or Gremlin were precipitated with a monoclonal antibody directed against their C-terminal MYC tags. Taken together, these results demonstrate a direct physical interaction between DAN-family members and BMP-2.

To further characterize the interaction between BMPs and their antagonists, we determined whether Noggin could compete with each family member for binding to BMP-2. We found that the addition of 2 or 10 μg purified Noggin blocks the interaction between Cerberus, Gemlin, or DAN and BMP-2. Noggin's ability to block the association between DAN-family members and BMP-2 adds to the evidence that these interactions are specific, and further indicates that DAN-family members and Noggin all bind a similar domain on BMP-2.

Cerberus Blocks Signaling by Activin and Xnr-2. The sequence divergence within the DAN family is reminiscent of the divergence within the TGF-β family, and suggested that individual DAN-family members might antagonize different subsets of TGF-β ligands. Since radial expression of Cerberus suppresses formation of trunk-tail mesoderm (Bouwmeester et al., 1996), we tested the possibility that it might block the action of mesoderm-inducing TGF-β ligands like Activin, BVg-1, and Xnr-2 (Smith et al., 1990; Thomsen et al., 1990; Thomsen and Melton, 1993; Jones et al., 1995). Animal caps were isolated from embryos coinjected with Activin (1 pg), BVg-1 (100 pg), or Xnr-2 (100 pg) mRNA, and 1 ng of Gremlin, Cerberus, or DAN mRNA, and were then analyzed for induction of the pan-mesodermal marker Xbra (Smith et al., 1991). We found that Cerberus expression significantly reduced or completely eliminated Xbra induction by Activin or Xnr-2. In contrast, neither Gremlin nor DAN blocked Xbra induction despite their doses being well above those required for biological activity in other assays. The lack of mesoderm induction in Cerberus-injected caps is not due to their inability to become mesodermalized since Xbra was induced in explants coinjected with Smad-2(C), a Smad-2-β-Galactosidase fusion protein that induces mesoderm in a ligand-independent fashion (Baker and Harland, 1996). Thus, unlike other DAN-family members, Cerberus antagonizes the activity of both BMPs and Activin-like ligands.

The Gremlin cDNA encodes a secreted protein whose activities are similar to those of the previously identified BMP antagonists Noggin, Chordin and Follistatin (Reviewed in Harland and Gerhart, 1997; Sasai and De Robertis, 1997). Like these factors, Gremlin antagonizes BMP activity in multiple assays, and it is able to physically associate with BMP-2. Despite these functional similarities, Gremlin has no sequence similarity to previously-identified BMP antagonists, and it is not expressed in the organizer. Instead, zygotic Gremlin transcripts are largely limited to the neural crest and its derivatives. This expression pattern shows that organizer-like activities are not restricted to the gastrulating embryo, and indicates that these inductive signals are used broadly in development.

Gremlin's acts as an essential modulator of BMP signaling in neural crest cells, preventing, premature or excessive exposure to BMP signals during their birth and subsequent migration. Consistently, BMP-2, BMP-4, and Gremlin are expressed at similar times and places during embryonic development. At tailbud stages, BMP-2 and BMP-4 are expressed in a coincident pattern in the fin neural crest (Clement et al., 1995; Hemmati-Brivanlou and Thomsen, 1995; Schmidt et al., 1995). BMP-4 is also expressed in the roof plate of the spinal cord (Fainsod et al., 1994). By modulating these signals, Gremlin has an important role in determining the timing of neural crest cell differentiation and/or the choice of differentiated fates.

While members of the DAN family have no sequence similarity to Noggin or Chordin, their activities indicate that they antagonize BMP signaling using the same mechanism. Support for this model comes from the finding that Gremlin, Cerberus and DAN all bind BMP-2. Furthermore, Noggin effectively competes with DAN-family members for binding to BMP-2, indicating that the interaction between a BMP and its antagonists occurs through a similar BMP domain.

Thus, despite the lack of sequence similarity, Noggin, Gremlin, and by extension, all BMP antagonists, share structural similarities that allow them to interact with similar domains on their cognate BMPs.

The scope of TGF-β antagonizing activities of the DAN family is broadened by the finding that Cerberus also blocks signaling by Activin and Nodal-like ligands. In their original study, Bouwmeester et al. (1996) found that radial expression of Cerberus blocked formation of trunk/tail mesoderm and prechordal plate mesoderm. We extended this finding by showing that among DAN-family members, only Cerberus antagonizes the mesoderm-inducing activity of Xnr-2 and Activin. Thus, despite their structural similarities, DAN-family members have specificity for different TGF-β signals. We conclude that DAN-family members act by binding overlapping subsets of TGF-β ligands, preventing them from interacting with their cell surface receptors. The diverse activities of DAN-family members result from their ability to antagonize specific TGF-β signaling pathways required for embryonic inductions and cell proliferation. The different mRNA doses required for Gremlin, Cerberus, and DAN to neuralize animal cap ectoderm is consistent with the idea that they differ in their affinity for BMP-4. In addition, we have shown in additional binding studies that Gremlin and DAN have substantially different affinities for BMP-2.

Embryo Manipulations and RT-PCR. Xenopus embryos were generated and staged as described (Nieuwkoop and Faber, 1967; Condie and Harland, 1987). Ventral marginal zone (VMZ) assays were done by injecting the marginal zone of each blastomere of 4-cell embryos and then explanting, culturing and harvesting VMZs as described (Zimmerman et al., 1996). For animal cap assays, 1-cell embryos were injected in the animal pole. Animal caps were explanted at stage 8–9, cultured in 75% NAM (Peng, 1991) and harvested at stage 10.5–11, stage 22, or stage 27.

RT-PCR analysis was done as described (Wilson and Melton, 1994). Primer sets and PCR conditions for Xbra, Ef1-α, Muscle actin, and NCAM are described in Wilson and Melton (1994), and those for Edd, and Nkx 2.5 are described in Bouwmeester et al. (1996).

Construction of a Xenopus Ovary cDNA Library. Poly (A)+RNA was isolated from Xenopus ovaries by oligo(dT) cellulose selection from a proteinase K/SDS lysate (Badley et al., 1988). This mRNA was used synthesize a cDNA library containing ~650,000 independent clones using the SuperScript cDNA cloning system (Life Technologies). To maximize expression of inserts, we established the library in CS 105, a derivative of CS2+(Turner and Weintraub, 1994) that produces synthetic mRNAs with high activity. cDNA pools were made from 121 plates containing ~1000 colonies each.

Expression Cloning. To make transcription templates, cDNA pools were digested with Asc-1, followed by digestion with 0.2 mg/ml proteinase K, 0.5% SDS at 50° for 1 hr, phenol/chloroform extraction, and precipitation. Synthetic MnRNA was synthesized with the mMessage mMachine SP6 kit (Ambion). 1 ng of each MRNA pool was injected into the marginal zone of one ventral blastomere of a 4-cell embryo. Tadpole-stage embryos were scored for presence of a secondary axis. The Gremlin cDNA was isolated from an active pool by sib-selection (Smith and Harland, 1991).

In Sit Hybridization, Immunostaining, and Histology. Whole-mount in situ hybridization used standard methods (Lamb et al., 1993) . Sense and antisense probes were generated from the full length Gremlin cDNA. For histological analysis, stained embryos were embedded in paraplast, and 10–20 μm sections were cut.

The presence of neural tissue, muscle, and notochord in embryos was determined by immunostaining with the antibodies 6F11 (Lamb et al., 1993), 12/101 (Kintner and Brockes, 1984), and Tor70 (Bolce et al., 1992), respectively.

Identification of Gremlin Homologs. A chick Gremlin cDNA was isolated by probing a stage 12-15 chick embryonic cDNA library, with the Xenopus Gremlin cDNA under moderately stringent hybridization conditions (0.5 M $Na_2PO_4$ pH 7.2, 15% Formamide, 7% SDS, 1 mM EDTA, and 1% BSA, at 42°). A mouse genomic Gremlin clone was isolated from a 129SVJ genomic DNA library (Stratagene) in a similar fashion. A human Gremlin cDNA was identified in a BLAST search of the GenBank EST database (I.M.A.G.E. consortium clone ID 272074, GenBank accession N35377) (Altschul et al., 1990; Lennon et.al., 1996).

The mouse DAN clone was obtained as an EST (GenBank accession number AA008891). Xenopus Cerberus and DAN cDNAs were isolated from a stage 11 LiCl-treated gastrula library. ceGR-1 was identified in a BLAST search of C. elegans genomic DNA sequences, and a ceGR-1 cDNA fragment was then cloned from a him-8(e1489) embryonic cDNA library. The identity of all clones used in these experiments was confirmed by DNA sequence analysis.

Preparation of Secreted Proteins in Xenopus Oocytes. Oocytes were isolated from ovaries by treatment with 0.2% collagenase (Boehringer Mannheim), or by manual defolliculation. They were injected with 50 ng synthetic MnRNA and cultured at 20° in groups of 5 in 100 μL OR2 (Peng, 1991) supplemented with 0.5 mg/ml BSA, 100 μg/ml penicillin, 100 μg/ml streptomycin sulfate, and 30 μCi$^{35}$S-methionine. After 1 day, 10 μl of each supernatant was analyzed by SDS-PAGE followed by fluorography.

Production of DAN-family COS Cell Supernatants. Conditioned COS supernatants were made by transfecting COS7 cells ($3.5\times10^6$/150 mm plate initial seeding density) with plasmids encoding Xenopus or human Gremlin, mouse DAN, or human Cerberus using Lipofectamine (Life Technologies). Control media was made by transfecting the expression vector pMT21. For detection in Western blots, Gremlins and MDAN were fused to a C-terminal triple-MYC epitope tag. human Cerberus was fused to a C-terminal FLAG epitope tag. xGremlin supernatants were quantified by comparison with known amounts of bacterially-expressed His-tagged Gremlin purified on a Ni-NTA-agarose column (Qiagen). In embryo assays, hCerberus-FLAG mRNA has comparable activities to Xenopus Cerberus mRNA. xQremlin-$MYC_3$ mRNA behaves like its wild-type counterpart.

Immunoprecipitation and Immunoblotting. Initially, 250–1000 μl of a hCerberus-FLAG, mDAN-$MYC_3$, or xGremlin-$MYC_3$ COS supernatant was incubated with 1 μg BMP-2 in the presence of protein G sepharose beads bound to the BMP-2,4-specific monoclonal antibody h3b2 in 1 ml of binding buffer (25 mM HEPES pH 7.7, 0.2 M KCl, 12.5 mM $MgCl_2$, 0.1 mM EDTA, 0.1% BSA, 0.1%NP40, 0.2 mM PMSF) overnight at 4°. Beads were washed twice in binding buffer, boiled in loading dye, and analyzed by Western blot. Tagged proteins were detected using monoclonal antibodies directed against the FLAG epitope (M2, Kodak), or against the MYC epitope (9E10), and a peroxidase-conjugated secondary antibody (Pierce). Competition experiments were done by adding 2 or 10 μg purified Xenopus Noggin to the binding reaction.

In reciprocal binding experiments, 1 μg hCerberus or hGremlin-$MYC_3$, or 1 ml of a mDAN-$MYC_3$ COS supernatant was incubated with 0.5–1 μg BMP-2 in the presence of 0.1% Tween-20, 1 M NaCl, or 0.1% NP-40+0.2 M KCl, respectively. hCerberus was immunoprecipitated using protein G sepharose beads bound to anti-hCerberus polyclonal antibodies. hGremlin-$MYC_3$ and mDAN-$MYC_3$ were immunoprecipitated using 9E10 beads. Competition experiments were done by adding 2 or 10 μg human Noggin. The presence of coprecipitating BMP-2 was assessed on Western blots using a polyclonal antibody directed against BMP-2.

Protocol for high throughput human gremlin—BMP binding assay.

A. Reagents:

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM $MgCl_2$, 1% glycerol, 0.5% NP-40, 50 mM β-mercaptoethanol, 1 mg/ml BSA, cocktail of protease inhibitors.

$^{33}$P human gremlin protein 10×stock: $10^{-8}$–$10^{-6}$M "cold" human gremlin supplemented with 200,000–250,000 cpm of labeled human gremlin (Beckman counter). Place in the 4° C. microfridge during screening.

Protegse inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2mM $NaVo_3$ (Sigma #S-6508) in 10 ml of PBS.

BMP: $10^{-7}$–$10^{-4}$ M biotinylated BMP in PBS.

B. Preparation of assay plates:

Coat with 120 μl of stock N-Avidin per well overnight at 4° C.

Wash 2 times with 200 μl PBS.

Block with 150 μl of blocking buffer.

Wash 2 times with 200 μl PBS.

C. Assay:

Add 40 μl assay buffer/well.

Add 10 μl compound or extract.

Add 10 μl $^{33}$P-gremlin protein (20–25,000 cpm/0.1–10 pmoles/well=$10^{-9}$–$10^{-7}$ M fin conc).

Shake at 25° C. for 15 minutes.

Incubate additional 45 minutes at 25° C.

Add 40 μl biotinylated BMP (0.1–10 pmoles/40 μl in assay buffer)

Incubate 1 hour at room temperature.

Stop the reaction by washing 4 times with 200 μl PBS.

Add 150 μl scintillation cocktail.

Count in Topcount.

D. Controls for all assays (located on each plate):

a. Non-specific binding b. Soluble (non-biotinylated gremlin) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for reducing morphogen-dependent bone formation of a cell comprising an extracellular surface in contact with a medium, said method comprising the step of:
contacting said medium with an antagonist of a bone morphogenic protein (BMP) selected from the group consisting of human BMP2 and human BMP4, said antagonist produced exogenously from said cell and comprising SEQ ID NO:2, 4, 6, 8 or 9 or a deletion mutant of a sequence selected from the group consisting of SEQ ID NO:2 or 8 wherein said deletion mutant encodes a polypeptide that retains at least residues 64–179 of SEQ ED NO:2 or residues 28–176 of SEQ ID NO:8 and is sufficient to specifically bind and antagonize said BUT, under conditions whereby said morphogen-dependent bone formation is reduced; and
measuring a resultant reduction of said morphogen-dependent bone formation.

2. A Method according to claim 1, wherein said sequence is SEQ ID NO:8.

3. A method according to claim 1, wherein said deletion mutant is selected from:
DΔN1 (SEQ ID NO:8, residues 3–181); DΔC4 (SEQ ID NO:8, residues 1–177);
DΔN2 (SEQ ID NO:8, residues 8–181); DΔC5 (SEQ ID NO:8, residues 1–176);
DΔN3 (SEQ ID NO:8, residues 18–181); DΔNC1 (SEQ ID NO:8, residues 3–180);
DΔN4 (SEQ ID NO:8, residues 23–181); DΔNC2 (SEQ ID NO:8, residues 2–177);
DΔN5 (SEQ ID NO:8, residues 28–181); DΔNC3 (SEQ ID NO:8, residues 7–179);
DΔC1 (SEQ ID NO:8, residues 1–180); DΔNC4 (SEQ ID NO:8, residues 16–180);
DΔC2 (SEQ ID NO:8, residues 1–179); DΔNC5 (SEQ ID NO:8, residues 21–178) and
DΔC3 (SEQ ID NO:8, residues 1–178).

4. A method according to claim 1, wherein said antagonist comprises SEQ ID NO:4.

5. A method according to claim 1, wherein said antagonist comprises SEQ ID NO:6.

6. A method according to claim 1, wherein said antagonist comprises SEQ ID NO:8.

7. A method according to claim 1, wherein said antagonist comprises SEQ ID NO:9.

8. A method according to claim 1, wherein said cell is in situ and said medium is a physiological fluid comprising said BMP.

9. A method for reducing morphogen-dependent bone formation of a cell comprising an extracellular surface in contact with a medium, said method comprising the step of contacting said medium with an antagonist of a bone morphogenic protein (BMP) selected from the group consisting of human BMP2 and human BMP4, said antagonist produced exogenously from said cell and comprising SEQ ID NO:2 or a deletion mutant of SEQ ID NO:2 wherein said deletion mutant encodes a polypeptide that retains at least residues 64–179 of SEQ ID NO:2 and is sufficient to specifically bind and antagonize said BMP, under conditions whereby said morphogen-dependent bone formation is reduced; and
measuring a resultant reduction of said morphogen-dependent bone formation.

10. A method according to claim 2, wherein said cell is in situ and said medium is a physiological fluid comprising said BMP.

11. A method according to claim 9, wherein said deletion mutant is selected from:
GΔN1 (SEQ ID NO:2, residues 2–184); GΔC4 (SEQ ID NO:2, residues 1–180);
GΔN2 (SEQ ID NO:2, residues 12–184); GΔC5 (SEQ ID NO:2, residues 1–179);
GΔN3 (SEQ ID NO:2, residues 24–184); GΔNC1 (SEQ ID NO:2, residues 21–181);
GΔN4 (SEQ ID NO:2, residues 48–184); GΔNC2 (SEQ ID NO:2, residues 34–182);
GΔN5 (SEQ ID NO:2, residues 64–184); GΔNC3 (SEQ ID NO:2, residues 57–183);
GΔC1 (SEQ ID NO:2, residues 1–183); GΔNC4 (SEQ ID NO:2, residues 13–183);

GΔC2 (SEQ ID NO:2, residues 1–182); GΔNC5 (SEQ ID NO:2, residues 45–181); and

GΔC3 (SEQ ID NO:2, residues 1–181).

12. A method according to claim 9, wherein said cell is in situ and said medium is a physiological fluid comprising said BMP.

13. A method according to claim 10, wherein said cell is in situ and said medium is a physiological fluid comprising said BMP.

14. A method according to claim 3, wherein said cell is in situ and said medium is a physiological fluid comprising said BMP.

15. A method according to claim 4, wherein said cell is in situ and said medium is a physiological fluid comprising said BMP.

16. A method according to claim 5, wherein said cell is in situ and said medium is a physiological fluid comprising said BMP.

17. A method according to claim 6, wherein said cell is in situ and said medium is a physiological fluid comprising said BMP.

18. A method according to claim 5, wherein said cell is in situ and said medium is a physiological fluid comprising said BMP.

19. A method for reducing morphogen-dependent bone formation of a cell comprising an extracellular surface in contact with a medium, said method comprising the step of:

contacting said medium with an antagonist of a bone morphogenic protein (BMP) selected from the group consisting of human BMP2 and human BMP4, said antagonist produced exogenously from said cell and comprising SEQ ID NO:2, under conditions whereby said morphogen-dependent bone formation is reduced; and measuring a resultant reduction of said morphogen-dependent bone formation.

20. A method according to claim 19, wherein said cell is in situ and said medium is a physiological fluid comprising said BMP.

* * * * *

UNITED STATES PATENT AND TRADEMARK OFFICE
CERTIFICATE OF CORRECTION

PATENT NO. : 6,432,410 B1
DATED : August 13, 2002
INVENTOR(S) : Harland et al.

Page 1 of 1

It is certified that error appears in the above-identified patent and that said Letters Patent is hereby corrected as shown below:

Column 37,
Line 37, "BUT" should read -- BMP --

Column 39,
Line 8, change "10" to -- 11 --

Column 40,
Line 1, change "5" to -- 7 --

Signed and Sealed this

Twenty-fourth Day of December, 2002

JAMES E. ROGAN
*Director of the United States Patent and Trademark Office*

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 619 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 47..598

(xi) SEQUENCE DESCRIPTION: SEQ ID NO: 1:

```
CCACGCGTCG AAAGCGCAGG CCCCGAGGAC CCGCCGCACT GACAGT ATG AGC CGC         55
                                                   Met Ser Arg
                                                     1

ACA GCC TAC ACG GTG GGA GCC CTG CTT CTC CTC TTG GGG ACC CTG CTG       103
Thr Ala Tyr Thr Val Gly Ala Leu Leu Leu Leu Leu Gly Thr Leu Leu
      5                  10                  15

CCG GCT GCT GAA GGG AAA AAG AAA GGG TCC CAA GGT GCC ATC CCC CCG       151
Pro Ala Ala Glu Gly Lys Lys Lys Gly Ser Gln Gly Ala Ile Pro Pro
 20                  25                  30                  35

CCA GAC AAG GCC CAG CAC AAT GAC TCA GAG CAG ACT CAG TCG CCC CAG       199
Pro Asp Lys Ala Gln His Asn Asp Ser Glu Gln Thr Gln Ser Pro Gln
                 40                  45                  50

CAG CCT GGC TCC AGG AAC CGG GGG CGG GGC CAA GGG CGG GGC ACT GCC       247
Gln Pro Gly Ser Arg Asn Arg Gly Arg Gly Gln Gly Arg Gly Thr Ala
             55                  60                  65

ATG CCC GGG GAG GAG GTG CTG GAG TCC AGC CAA GAG GCC CTG CAT GTG       295
Met Pro Gly Glu Glu Val Leu Glu Ser Ser Gln Glu Ala Leu His Val
         70                  75                  80

ACG GAG CGC AAA TAC CTG AAG CGA GAC TGG TGC AAA ACC CAG CCG CTT       343
Thr Glu Arg Lys Tyr Leu Lys Arg Asp Trp Cys Lys Thr Gln Pro Leu
     85                  90                  95

AAG CAG ACC ATC CAC GAG GAA GGC TGC AAC AGT CGC ACC ATC ATC AAC       391
Lys Gln Thr Ile His Glu Glu Gly Cys Asn Ser Arg Thr Ile Ile Asn
100                 105                 110                 115

CGC TTC TGT TAC GGC CAG TGC AAC TCT TTC TAC ATC CCC AGG CAC ATC       439
Arg Phe Cys Tyr Gly Gln Cys Asn Ser Phe Tyr Ile Pro Arg His Ile
                120                 125                 130

CGG AAG GAG GAA GGT TCC TTT CAG TCC TGC TCC TTC TGC AAG CCC AAG       487
Arg Lys Glu Glu Gly Ser Phe Gln Ser Cys Ser Phe Cys Lys Pro Lys
            135                 140                 145

AAA TTC ACT ACC ATG ATG GTC ACA CTC AAC TGC CCT GAA CTA CAG CCA       535
Lys Phe Thr Thr Met Met Val Thr Leu Asn Cys Pro Glu Leu Gln Pro
        150                 155                 160

CCT ACC AAG AAG AAG AGA GTC ACA CGT GTG AAG CAG TGT CGT TGC ATA       583
Pro Thr Lys Lys Lys Arg Val Thr Arg Val Lys Gln Cys Arg Cys Ile
    165                 170                 175

TCC ATC GAT TTG GAT TAAGCCAAAT CCATGCACCA G                           619
Ser Ile Asp Leu Asp
180
```

(2) INFORMATION FOR SEQ ID NO: 2:

(i) SEQUENCE CHARACTERISTICS:
    (A) LENGTH: 184 amino acids
    (B) TYPE: amino acid
    (D) TOPOLOGY: linear (ii) MOLECULE TYPE: protein (xi) SEQUENCE DESCRIPTION: SEQ ID NO: 2:

Met Ser Arg Thr Ala Tyr Thr Val Gly Ala Leu Leu Leu Leu Gly
 1               5                  10                  15

Thr Leu Pro Ala Ala Glu Gly Lys Lys Lys Gly Ser Gln Gly Ala
                20                  25                  30

Ile Pro Pro Asp Lys Ala Gln His Asn Asp Ser Glu Gln Thr Gln
            35                  40                  45

Ser Pro Gln Gln Pro Gly Ser Arg Asn Arg Gly Arg Gly Gln Gly Arg
 50                  55                  60

Gly Thr Ala Met Pro Gly Glu Glu Val Leu Glu Ser Ser Gln Glu Ala
 65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
                100                 105                 110

Ile Ile Asn Arg Phe Cys Tyr Gly Gln Cys Asn Ser Phe Tyr Ile Pro
            115                 120                 125

Arg His Ile Arg Lys Glu Glu Gly Ser Phe Gln Ser Cys Ser Phe Cys
 130                 135                 140

Lys Pro Lys Lys Phe Thr Thr Met Met Val Thr Leu Asn Cys Pro Glu
145                 150                 155                 160

Leu Gln Pro Pro Thr Lys Lys Lys Arg Val Thr Arg Val Lys Gln Cys
                165                 170                 175

Arg Cys Ile Ser Ile Asp Leu Asp
                180

(2) INFORMATION FOR SEQ ID NO: 3:

(i) SEQUENCE CHARACTERISTICS:
        (A) LENGTH: 1781 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 66..611

(xi) SEQUENCE DESCRIPTION: SEQ ID NO: 3:

CCCGTGTAGC AGCCTCACAT GGACTAGTCT TGATCTGCTG TGAGCCAGCG GCCCCTTCCC      60

ACAGG ATG AAC TGT CTC GTT TAT GCT CTA GGA TCC CTT TTC CTT CTG        107
      Met Asn Cys Leu Val Tyr Ala Leu Gly Ser Leu Phe Leu Leu
          185                 190                 195

AGT GGG CTC CTC CTC CCC AGC TCC GAA GGG AAG AAG AAG GTT AGT GGA      155
Ser Gly Leu Leu Leu Pro Ser Ser Glu Gly Lys Lys Lys Val Ser Gly
            200                 205                 210

TCA CAG GGA GCC ATT CCT CCC CCT GAC AAA GGG CAG CCC AAT GAC TCT      203
Ser Gln Gly Ala Ile Pro Pro Pro Asp Lys Gly Gln Pro Asn Asp Ser
215                 220                 225                 230

GAG CAA GGT CAA GCT CAG CCA GGA GAC CGG GTC AGA GGG AAG GGG AAG      251
Glu Gln Gly Gln Ala Gln Pro Gly Asp Arg Val Arg Gly Lys Gly Lys
                235                 240                 245

```
GGA CAA GCA CTA GCG GCT GAA GAA GTG CTG GAG TCC AGT CAA GAA GCT      299
Gly Gln Ala Leu Ala Ala Glu Glu Val Leu Glu Ser Ser Gln Glu Ala
            250                 255                 260

CTA CAC GTC ACT GAA CGC AAG TAT CTA AAG AGG GAC TGG TGT AAG ACT      347
Leu His Val Thr Glu Arg Lys Tyr Leu Lys Arg Asp Trp Cys Lys Thr
            265                 270                 275

CAG CCC TTA AAG CAA ACA ATT CAC GAG GAC GGG TGC AAC AGT CGT ACC      395
Gln Pro Leu Lys Gln Thr Ile His Glu Asp Gly Cys Asn Ser Arg Thr
            280                 285                 290

ATC ATC AAC CGC TTC TGC TAT GGG CAA TGC AAC TCC TTC TAC ATC CCC      443
Ile Ile Asn Arg Phe Cys Tyr Gly Gln Cys Asn Ser Phe Tyr Ile Pro
295                 300                 305                 310

CGT CAC ATA CGC AGG GAG GAG GGC TCA TTT CAA TCC TGC TCC TTC TGC      491
Arg His Ile Arg Arg Glu Glu Gly Ser Phe Gln Ser Cys Ser Phe Cys
            315                 320                 325

AAG CCT AAA AAA TTC ACC ACA ATG GTG GTC ACC CTG AAC TGC CCA GAG      539
Lys Pro Lys Lys Phe Thr Thr Met Val Val Thr Leu Asn Cys Pro Glu
            330                 335                 340

CTA CAA CCT CCC ACA AAG AAG AAG AGA ATT ACA CGT GTC AAG CAG TGT      587
Leu Gln Pro Pro Thr Lys Lys Lys Arg Ile Thr Arg Val Lys Gln Cys
            345                 350                 355

CGC TGC ATC TCC ATA GAC CTG GAC TAATGTGCCG CTGGGCCTGT GAATACTAGA     641
Arg Cys Ile Ser Ile Asp Leu Asp
            360                 365

ATAATGTACT GGGAGCTTCA CTCTTCATAT CCATACCATT ACTGTCTGTG CCAAGACCAT    701

CAAACCACAA TCCTCACAGG CATTCTGTTG TGTCCGAGCT ACTTTATGCT TTTCATGCTA    761

ATACACCATC AGCAGGAATC CAAACAAGCA ATAAATATCT AGATTTCCTC CTTCTGCTGA    821

ACTGTCCCGA ACAGCGTTGG GTTCTTTATC CTTTTTTTTA GGGAATGTGG AGGCCTGCAA    881

AGACGGCATC CATGTATACA TTGTGTACAT ATATATTATT TATTCTCACG TGTGTTTTTG    941

TGCACATAAA AGAGCATGAG AAAAGGCGCT GAGACTGATG AGAGTTAATG AATTGTGCAT   1001

GTTACTGGCA TGTAGCTGTG AGTCGCCACT ACAGGAGACC CAATATTAAG GCAATCTATG   1061

ACTTTCTGTA AGGTTCTCTG TGGGTAAACA TGCATTATCC ACAATACATT TTCTTATATG   1121

TGGGTTAATC TGCCACAAAC CTGGCAAATA TGGCAGTTTG AGGACAGAAA ATGCCATGTG   1181

AAGCATGTAC AGTCTAATCA TCGCAATATA TTTTTTAAAA CCATTGTGGC TGATTTGGGG   1241

GGTAAAGAGC AACACAATGC AGGGAAGTTC CCAGGAGTTG GGGAGACTAA TGGCATATTT   1301

CTCATGTATT GAAGACTGCC GGGAGAGAGA GAAGCAAACT GGTGCCAAAT GGCAGTGGAA   1361

AAAGAACGAG GAGGATGAGA TATTGAGGCA TTTTACTAGG GACTAGATTA CTGCAATTTA   1421

AAGTTGCTCT GACTCCTCTT ATTCACATTT GGGACTGTAG CAACAACAAC TCTGTGTCAT   1481

TTTATTGAGG TCAGGGGTGG GAAACAAATC ACTGCATGGC TGGTTATGTC CAGACAGAAC   1541

CACCCCAAAC CCCTCTCGCT TCCCAGAAAG TCCCACAACT GCAATCTGAG ACTGTCCCAG   1601

CAAAACAGGA CAATCTAGGG AAAATGCCAT TGCAATTGTA GTGTTGCACG ATAAACTGTT   1661

CCCTAAAAAA AAAATTATTT GTATTAAACA AATTAGCGCA GAAAGTTTGC CAATAATATG   1721

AGCTTCATGA TAAATAAAGA AACAGTACAA GATGGAAATA TTAAAAAAAA AAAAAAAAA    1781
```

(2) INFORMATION FOR SEQ ID NO: 4:

(i) SEQUENCE CHARACTERISTICS:
        (A) LENGTH: 182 amino acids
        (B) TYPE: amino acid
        (D) TOPOLOGY: linear -continued (ii) MOLECULE TYPE: protein (xi) SEQUENCE DESCRIPTION: SEQ ID NO: 4:

```
Met Asn Cys Leu Val Tyr Ala Leu Gly Ser Leu Phe Leu Leu Ser Gly
 1               5                   10                  15

Leu Leu Leu Pro Ser Ser Glu Gly Lys Lys Val Ser Gly Ser Gln
                20                  25                  30

Gly Ala Ile Pro Pro Asp Lys Gly Gln Pro Asn Asp Ser Glu Gln
            35                  40                  45

Gly Gln Ala Gln Pro Gly Asp Arg Val Arg Gly Lys Gly Lys Gly Gln
     50                  55                  60

Ala Leu Ala Ala Glu Glu Val Leu Glu Ser Ser Gln Glu Ala Leu His
 65                  70                  75                  80

Val Thr Glu Arg Lys Tyr Leu Lys Arg Asp Trp Cys Lys Thr Gln Pro
                 85                  90                  95

Leu Lys Gln Thr Ile His Glu Asp Gly Cys Asn Ser Arg Thr Ile Ile
                100                 105                 110

Asn Arg Phe Cys Tyr Gly Gln Cys Asn Ser Phe Tyr Ile Pro Arg His
            115                 120                 125

Ile Arg Arg Glu Glu Gly Ser Phe Gln Ser Cys Ser Phe Cys Lys Pro
130                 135                 140

Lys Lys Phe Thr Thr Met Val Val Thr Leu Asn Cys Pro Glu Leu Gln
145                 150                 155                 160

Pro Pro Thr Lys Lys Lys Arg Ile Thr Arg Val Lys Gln Cys Arg Cys
                165                 170                 175

Ile Ser Ile Asp Leu Asp
                180
```

(2) INFORMATION FOR SEQ ID NO: 5:

(i) SEQUENCE CHARACTERISTICS:
      (A) LENGTH: 811 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 104..655

(xi) SEQUENCE DESCRIPTION: SEQ ID NO: 5:

```
GAATTCGAGG ATCCGGGTAC CATGGCAGCG CTCAGCCCCG CCGCGCCCCG CCGAGGAGCC      60

GCCGCCGAGC CGGGCCCCCG AGGAGCAGCC GACGCCGCGC AGG ATG GTC CGC ACA       115
                                               Met Val Arg Thr
                                                       185

CTG TAT GCC ATC GGC GCT GTG TTT CTT CTG ACG GGA TTT CTG CTA CCG       163
Leu Tyr Ala Ile Gly Ala Val Phe Leu Leu Thr Gly Phe Leu Leu Pro
            190                 195                 200

ACA GCA GAA GGG AGA AAG AGG AAT CGT GGA TCT CAA GGC GCT ATC CCT       211
Thr Ala Glu Gly Arg Lys Arg Asn Arg Gly Ser Gln Gly Ala Ile Pro
            205                 210                 215

CCT CCT GAC AAG GAT CAG CCC AAT GAT TCA GAG CAG ATG CAG ACA CAG       259
Pro Pro Asp Lys Asp Gln Pro Asn Asp Ser Glu Gln Met Gln Thr Gln
        220                 225                 230

CAG CAG TCA GGC TCC AGG CAT CGA GAA AGA GGA AAA GGC ACC TCA ATG       307
Gln Gln Ser Gly Ser Arg His Arg Glu Arg Gly Lys Gly Thr Ser Met
235                 240                 245                 250
```

```
CCT GCT GAG GAG GTG CTG GAG TCC AGC CAG GAG GCA CTG CAC ATC ACT        355
Pro Ala Glu Glu Val Leu Glu Ser Ser Gln Glu Ala Leu His Ile Thr
            255                 260                 265

GAG CGC AAA TAC CTA AAA CGG GAT TGG TGC AAA ACT CAG CCC CTC AAA        403
Glu Arg Lys Tyr Leu Lys Arg Asp Trp Cys Lys Thr Gln Pro Leu Lys
            270                 275                 280

CAA ACT ATC CAT GAA GAA GGC TGC AAC AGT CGC ACC ATT ATC AAC AGG        451
Gln Thr Ile His Glu Glu Gly Cys Asn Ser Arg Thr Ile Ile Asn Arg
            285                 290                 295

TTC TGC TAT GGC CAA TGC AAT TCT TTC TAC ATC CCC AGG CAT GTC CGC        499
Phe Cys Tyr Gly Gln Cys Asn Ser Phe Tyr Ile Pro Arg His Val Arg
        300                 305                 310

AAA GAG GAA GGC TCT TTC CAG TCT TGT TCC TTC TGC AAG CCC AAG AAA        547
Lys Glu Glu Gly Ser Phe Gln Ser Cys Ser Phe Cys Lys Pro Lys Lys
315                 320                 325                 330

TTT ACC ACC ATG ACT GTT ACC CTC AAC TGC CCT GAG CTT CAG CCC CCT        595
Phe Thr Thr Met Thr Val Thr Leu Asn Cys Pro Glu Leu Gln Pro Pro
                335                 340                 345

AGG AAG AAG AAA AGA ATC ACC CGC GTG AAG GAG TGT CGG TGT ATA TCT        643
Arg Lys Lys Lys Arg Ile Thr Arg Val Lys Glu Cys Arg Cys Ile Ser
            350                 355                 360

ATC GAC TTG GAC TAAGCCGAGA AGTGCATTGT TCTGATTGCA CTCTGACTGT            695
Ile Asp Leu Asp
            365

CTGCAATCAT TGCCAGTGTG AGGGAGTGGC TTGAACTAGC AAAGCTTTGG GGCTGGATGA      755

AACTGAAAGG AACCCAGTGA ATCACCTAAA AAACTACAGC TAACTAAAAA AAAAAA          811

(2) INFORMATION FOR SEQ ID NO: 6:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO: 6:

Met Val Arg Thr Leu Tyr Ala Ile Gly Ala Val Phe Leu Leu Thr Gly
 1               5                  10                  15

Phe Leu Leu Pro Thr Ala Glu Gly Arg Lys Arg Asn Arg Gly Ser Gln
            20                  25                  30

Gly Ala Ile Pro Pro Asp Lys Asp Gln Pro Asn Asp Ser Glu Gln
        35                  40                  45

Met Gln Thr Gln Gln Ser Gly Ser Arg His Arg Glu Arg Gly Lys
    50                  55                  60

Gly Thr Ser Met Pro Ala Glu Glu Val Leu Glu Ser Ser Gln Glu Ala
65                  70                  75                  80

Leu His Ile Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
        115                 120                 125

Arg His Val Arg Lys Glu Glu Gly Ser Phe Gln Ser Cys Ser Phe Cys
    130                 135                 140

Lys Pro Lys Lys Phe Thr Thr Met Thr Val Thr Leu Asn Cys Pro Glu
145                 150                 155                 160

Leu Gln Pro Pro Arg Lys Lys Lys Arg Ile Thr Arg Val Lys Glu Cys
```

165                 170                 175
Arg Cys Ile Ser Ile Asp Leu Asp
                180

(2) INFORMATION FOR SEQ ID NO: 7:

(i) SEQUENCE CHARACTERISTICS:
        (A) LENGTH: 1929 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 59..601

(xi) SEQUENCE DESCRIPTION: SEQ ID NO: 7:

```
ACCCCCGCAC CCAGCTCCGC AGACCGGCGG GCGCGCGCGG GCTCTGGAGG CCACGGGC              58

ATG ATG CTT CGG GTC CTG GTG GGG GCT GTC CTC CCT GCC ATG CTA CTG             106
Met Met Leu Arg Val Leu Val Gly Ala Val Leu Pro Ala Met Leu Leu
185                 190                 195                 200

GCT GCC CCA CCA CCC ATC AAC AAG CTG GCA CTG TTC CCA GAT AAG AGT             154
Ala Ala Pro Pro Pro Ile Asn Lys Leu Ala Leu Phe Pro Asp Lys Ser
                205                 210                 215

GCC TGG TGC GAA GCC AAG AAC ATC ACC CAG ATC GTG GGC CAC AGC GGC             202
Ala Trp Cys Glu Ala Lys Asn Ile Thr Gln Ile Val Gly His Ser Gly
                220                 225                 230

TGT GAG GCC AAG TCC ATC CAG AAC AGG GCG TGC CTA GGA CAG TGC TTC             250
Cys Glu Ala Lys Ser Ile Gln Asn Arg Ala Cys Leu Gly Gln Cys Phe
                235                 240                 245

AGC TAC AGC GTC CCC AAC ACC TTC CCA CAG TCC ACA GAG TCC CTG GTT             298
Ser Tyr Ser Val Pro Asn Thr Phe Pro Gln Ser Thr Glu Ser Leu Val
                250                 255                 260

CAC TGT GAC TCC TGC ATG CCA GCC CAG TCC ATG TGG GAG ATT GTG ACG             346
His Cys Asp Ser Cys Met Pro Ala Gln Ser Met Trp Glu Ile Val Thr
265                 270                 275                 280

CTG GAG TGC CCG GGC CAC GAG GAG GTG CCC AGG GTG GAC AAG CTG GTG             394
Leu Glu Cys Pro Gly His Glu Glu Val Pro Arg Val Asp Lys Leu Val
                285                 290                 295

GAG AAG ATC CTG CAC TGT AGC TGC CAG GCC TGC GGC AAG GAG CCT AGT             442
Glu Lys Ile Leu His Cys Ser Cys Gln Ala Cys Gly Lys Glu Pro Ser
                300                 305                 310

CAC GAG GGG CTG AGC GTC TAT GTG CAG GGC GAG GAC GGG CCG GGA TCC             490
His Glu Gly Leu Ser Val Tyr Val Gln Gly Glu Asp Gly Pro Gly Ser
                315                 320                 325

CAG CCC GGC ACC CAC CCT CAC CCC CAT CCC CAC CCC CAT CCT GGC GGG             538
Gln Pro Gly Thr His Pro His Pro His Pro His Pro His Pro Gly Gly
                330                 335                 340

CAG ACC CCT GAG CCC GAG GAC CCC CCT GGG GCC CCC CAC ACA GAG GAA             586
Gln Thr Pro Glu Pro Glu Asp Pro Pro Gly Ala Pro His Thr Glu Glu
345                 350                 355                 360

GAG GGG GCT GAG GAC TGAGGCCCCC CCAACTCTTC CTCCCCTCTC ATCCCCTGT              641
Glu Gly Ala Glu Asp
                365

GGAATGTTGG GTCTCACTCT CTGGGGAAGT CAGGGGAGAA GCTGAAGCCC CCCTTTGGCA           701

CTGGATGGAC TTGGCTTCAG ACTCGGACTT GAATGCTGCC CGGTTGCCAT GGAGATCTGA           761

AGGGGCGGGG TTAGAGCCAA GCTGCACAAT TTAATATATT CAAGAGTGGG GGGAGGAAGC           821

AGAGGTCTTC AGGGCTCTTT TTTTGGGGGG GGGGTGGTCT CTTCCTGTCT GGCTTCTAGA           881
```

-continued

```
GATGTGCCTG TGGGAGGGGG AGGAAGTTGG CTGAGCCATT GAGTGCTGGG GGAGGCCATC    941

CAAGATGGCA TGAATCGGGC TAAGGTCCCT GGGGGTGCAG ATGGTACTGC TGAGGTCCCG   1001

GGCTTAGTGT GAGCATCTTG CCAGCCTCAG GCTTGAGGGA GGGCTGGGCT AGAAAGACCA   1061

CTGGCAGAAA CAGGAGGCTC CGGCCCCACA GGTTTCCCCA AGGCCTCTCA CCCCACTTCC   1121

CATCTCCAGG GAAGCGTCGC CCCAGTGGCA CTGAAGTGGC CCTCCCTCAG CGGAGGGGTT   1181

TGGGAGTCAG GCCTGGGCAG GACCCTGCTG ACTCGTGGCG CGGGAGCTGG GAGCCAGGCT   1241

CTCCGGGCCT TTCTCTGGCT TCCTTGGCTT GCCTGGTGGG GGAAGGGGAG GAGGGGAAGA   1301

AGGAAAGGGA AGAGTCTTCC AAGGCCAGAG GGAGGGGGAC AACCCCCCAA GACCATCCCT   1361

GAAGACGAGC ATCCCCCTCC TCTCCCTGTT AGAAATGTTA GTGCCCCGCA CTGTGCCCCA   1421

AGTTCTAGGC CCCCCAGAAA GCTGTCAGAG CCGGCCGCCT TCTCCCCTCT CCCAGGGATG   1481

CTCTTTGTAA ATATCGGATG GGTGTGGGAG TGAGGGGTTA CCTCCCTCGC CCCAAGGTTC   1541

CAGAGGCCCT AGGCGGGATG GGCTCGCTGA ACCTCGAGGA ACTCCAGGAC GAGGAGGACA   1601

TGGGACTTGC GTGGACAGTC AGGGTTCACT TGGGCTCTCT CTAGCTCCCC AATTCTGCCT   1661

GCCTCCTCCC TCCCAGCTGC ACTTTAACCC TAGAAGGTGG GGACCTGGGG GGAGGGACAG   1721

GGCAGGCGGC CCCATGAAGA AAGCCCCTCG TTGCCCAGCA CTGTCTGCGT CTGCTCTTCT   1781

GTGCCCAGGG TGGCTGCCAG CCCACTGCCT CCTGCCTGGG GTGGCCTGGC CCTCCTGGCT   1841

GTTGCGACGC GGGCTTCTGG AGCTTGTCAC CATTGGACAG TCTCCCTGAT GGACCCTCAG   1901

TCTTCTCATG AATAAATTCT TCGGAATT                                      1929
```

(2) INFORMATION FOR SEQ ID NO: 8:

(i) SEQUENCE CHARACTERISTICS:
        (A) LENGTH: 181 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Met Leu Arg Val Leu Val Gly Ala Val Leu Pro Ala Met Leu Leu
 1               5                  10                  15

Ala Ala Pro Pro Pro Ile Asn Lys Leu Ala Leu Phe Pro Asp Lys Ser
                20                  25                  30

Ala Trp Cys Glu Ala Lys Asn Ile Thr Gln Ile Val Gly His Ser Gly
            35                  40                  45

Cys Glu Ala Lys Ser Ile Gln Asn Arg Ala Cys Leu Gly Gln Cys Phe
        50                  55                  60

Ser Tyr Ser Val Pro Asn Thr Phe Pro Gln Ser Thr Glu Ser Leu Val
65                  70                  75                  80

His Cys Asp Ser Cys Met Pro Ala Gln Ser Met Trp Glu Ile Val Thr
                85                  90                  95

Leu Glu Cys Pro Gly His Glu Glu Val Pro Arg Val Asp Lys Leu Val
               100                 105                 110

Glu Lys Ile Leu His Cys Ser Cys Gln Ala Cys Gly Lys Glu Pro Ser
           115                 120                 125

His Glu Gly Leu Ser Val Tyr Val Gln Gly Glu Asp Gly Pro Gly Ser
       130                 135                 140

Gln Pro Gly Thr His Pro His Pro His Pro His Pro His Pro Gly Gly
145                 150                 155                 160
```

Gln Thr Pro Glu Pro Glu Asp Pro Pro Gly Ala Pro His Thr Glu Glu
                165                 170                 175

Glu Gly Ala Glu Asp
            180

(2) INFORMATION FOR SEQ ID NO: 9:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO: 9:

Met Asn Arg Thr Ala Tyr Thr Val Gly Ala Leu Leu Leu Leu Leu Gly
 1               5                  10                  15

Thr Leu Pro Thr Ala Glu Gly Lys Lys Lys Gly Ser Gln Gly Ala
                20                  25                  30

Ile Pro Pro Asp Lys Ala Gln His Asn Asp Ser Glu Gln Thr Gln
        35                  40                  45

Ser Pro Gln Pro Gly Ser Arg Thr Arg Gly Arg Gly Gln Gly Arg
    50                  55                  60

Gly Thr Ala Met Pro Gly Glu Glu Val Leu Glu Ser Ser Gln Glu Ala
 65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
                100                 105                 110

Ile Ile Asn Arg Phe Cys Tyr Gly Gln Cys Asn Ser Phe Tyr Ile Pro
                115                 120                 125

Arg His Ile Arg Lys Glu Glu Gly Ser Phe Gln Ser Cys Ser Phe Cys
            130                 135                 140

Lys Pro Lys Lys Phe Thr Thr Met Met Val Thr Leu Asn Cys Pro Glu
145                 150                 155                 160

Leu Gln Pro Pro Thr Lys Lys Arg Val Thr Arg Val Lys Gln Cys
                165                 170                 175

Arg Cys Ile Ser Ile Asp Leu Asp
            180

(2) INFORMATION FOR SEQ ID NO: 10:

(i) SEQUENCE CHARACTERISTICS:
        (A) LENGTH: 97 amino acids
        (B) TYPE: amino acid
        (D) TOPOLOGY: linear (ii) MOLECULE TYPE: protein (xi) SEQUENCE DESCRIPTION: SEQ ID NO: 10:

Lys Ser Ala Trp Cys Glu Ala Lys Asn Ile Thr Gln Ile Val Gly His
 1               5                  10                  15

Ser Gly Cys Glu Ala Lys Ser Ile Gln Asn Arg Ala Cys Leu Gly Gln
                20                  25                  30

Cys Phe Ser Tyr Ser Val Pro Asn Thr Phe Pro Gln Ser Thr Glu Ser
            35                  40                  45

Leu Val His Cys Asp Ser Cys Met Pro Ala Gln Ser Met Trp Glu Ile
        50                  55                  60

Val Thr Leu Glu Cys Pro Asp His Glu Glu Val Pro Arg Val Asp Lys

```
                65                  70                  75                  80
Leu Val Glu Lys Ile Val His Cys Ser Cys Gln Ala Cys Gly Lys Glu
                    85                  90                  95
Pro
```

(2) INFORMATION FOR SEQ ID NO: 11:

(i) SEQUENCE CHARACTERISTICS:
        (A) LENGTH: 97 amino acids
        (B) TYPE: amino acid
        (D) TOPOLOGY: linear (ii) MOLECULE TYPE: protein (xi) SEQUENCE DESCRIPTION: SEQ ID NO: 11:

```
Lys Ser Ala Trp Cys Glu Ala Lys Asn Ile Thr Gln Ile Val Gly His
 1               5                  10                  15

Ser Gly Cys Glu Ser Lys Ser Ile Gln Asn Arg Ala Cys Leu Gly Gln
                    20                  25                  30

Cys Phe Ser Tyr Ser Val Pro Asn Thr Phe Pro Gln Ser Thr Glu Ser
                35                  40                  45

Leu Val His Cys Asp Ser Cys Met Pro Ile Asp Ser Val Trp Asp Val
            50                  55                  60

Val Thr Leu Glu Cys Pro Gly Asn Glu Glu Phe Pro Arg Val Asp Lys
65                  70                  75                  80

Leu Val Glu Lys Ile Leu Gln Cys Ser Cys Gln Ala Cys Gly Lys Glu
                    85                  90                  95

Leu
```

(2) INFORMATION FOR SEQ ID NO: 12:

(i) SEQUENCE CHARACTERISTICS:
        (A) LENGTH: 90 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Lys Glu Ala Cys Lys Thr Leu Pro Phe Thr Gln Asn Ile Val His
 1               5                  10                  15

Glu Asn Cys Asp Arg Met Val Ile Gln Asn Asn Leu Cys Phe Gly Lys
                    20                  25                  30

Cys Ile Ser Leu His Val Pro Asn Gln Gln Asp Arg Arg Asn Thr Cys
                35                  40                  45

Ser His Cys Leu Pro Ser Lys Phe Thr Leu Asn His Leu Thr Leu Asn
            50                  55                  60

Cys Thr Gly Ser Lys Asn Val Val Lys Val Val Met Met Val Glu Glu
65                  70                  75                  80

Cys Thr Cys Glu Ala His Lys Ser Asn Phe
                85                  90
```

(2) INFORMATION FOR SEQ ID NO: 13:

(i) SEQUENCE CHARACTERISTICS:
        (A) LENGTH: 98 amino acids
        (B) TYPE: amino acid
        (D) TOPOLOGY: linear (ii) MOLECULE TYPE: protein (xi) SEQUENCE DESCRIPTION: SEQ ID NO: 13:

```
Met Asn Gln Arg Cys Asp Gly Gln Lys Phe Lys Gln Arg Ile Arg Val
 1               5                  10                 15
Asp Gly Cys Leu Thr Lys Val Val Val Asn Arg Leu Cys His Gly Ala
                20                  25                 30
Cys Ala Ser Ile Phe Ile Pro Arg Met His Ser Lys Lys Leu Lys Ala
             35                  40              45
Ala Phe Arg Ser Cys Ala Ala Cys Ala Pro Ala Glu Tyr Asp Tyr Val
         50              55                  60
Asp Ile Thr Leu Asp Cys Pro Gly Arg Thr Pro Pro Thr Ala Thr Lys
 65              70                  75                 80
Thr Ile Val Lys Val Lys Ser Cys Lys Cys Lys Glu Val Arg Ile Ala
                 85                  90                 95
Pro Phe
```